United States Patent [19]

Neelakantan

[11] Patent Number: 5,916,567
[45] Date of Patent: Jun. 29, 1999

[54] **HERBAL ANTI-DIABETIC THERAPEUTIC PRODUCT CONTAINING POWDERED *DOLICHOS BIFLORUS* SEEDS**

[75] Inventor: Kameswaran Neelakantan, T. Nagar Chennai, India

[73] Assignee: Gem Energy Industry Limited, Chennai, India

[21] Appl. No.: 08/984,253

[22] Filed: Dec. 3, 1997

[30] Foreign Application Priority Data

Jun. 20, 1997 [IN] India .............................. 1343/MAS/97

[51] Int. Cl.⁶ ............................ A61K 35/78; A61K 9/14; A23L 1/36
[52] U.S. Cl. ...................... 424/195.1; 424/489; 426/629; 514/866
[58] Field of Search ................ 424/195.1, 489; 426/629; 514/866

[56] References Cited

U.S. PATENT DOCUMENTS 4,156,721  5/1979  Gustowski et al. .................. 424/195.1
4,259,358  3/1981  Duthie ....................................... 426/26

FOREIGN PATENT DOCUMENTS 115321  12/1982  Poland .

*Primary Examiner*—Leon B. Lankford, Jr.
*Assistant Examiner*—Christopher R. Tate
*Attorney, Agent, or Firm*—Ladas & Parry

[57] ABSTRACT

A herbal anti-diabetic therapeutic product comprising from about 89.5–98.5% of powdered inner seed of *Dolichos biflorus* and from about 10.5–1.5% of powdered fibrous outer shell of the seed of *Dolichos biflorus* wherein the product is subjected to radiation for a period of 10–20 minutes.

9 Claims, No Drawings

HERBAL ANTI-DIABETIC THERAPEUTIC PRODUCT CONTAINING POWDERED *DOLICHOS BIFLORUS* SEEDS

This invention relates to an herbal therapeutic product for treating diabetes and a process for the manufacture of this novel product.

The invention relates to a product comprising, consisting essentially of or consisting of an active principle isolated from the seed of *Dolichos Biflorus*. The product is useful for controlling and treating the effects of diabetes.

BACKGROUND OF THE INVENTION

Diabetes mellitus is a chronic heredity disease which is characterized by an abnormally high level of glucose in the blood and in the urine. It is a disorder of carbohydrate metabolism.

Diabetes occurs at every age and in every race and is never cured though it may be controlled. It is a disease found throughout the world and may be related to certain geographic, environmental and socio-economic factors. There are variations in the pattern of the disease in different parts of the world.

Symptoms of diabetes fall into two main categories. Rapid epinephrine release causes sweating, tremors, tachycardia, anxiety and hunger. Central nervous system symptoms include dizziness, headaches, clouding of vision, blunted mental acuity, confusion, abnormal behavior, convulsions and loss of convulsions and loss of consciousness. When hypoglycemia is recurrent or severe, nervous system symptoms predominate, and the epinephrine phase may not be recognizable. With more rapid drops or wide swings in plasma glucose, adrenergic symptoms are predominant (Harrison's Principles of Internal Medicine, 11th Ed., McGraw-Hill Book Company, New York, 1987, p 1800).

Numerous strategies have been developed to achieve the goal of controlling diabetes like the use of open looped continuous subcutaneous pumps and multiple daily injections of insulin. With this continuous treatment the patients have to measure their blood sugar level to assure that close to normal blood sugar levels are maintained.

The treatment of diabetes was revolutionized with the discovery of insulin in 1921 and treatment was further modified after the introduction of oral drugs. However it has been found that intensive insulin treatment while it markedly delays and lessens long term retinal, nephrologic and neuropathic disease, leads to a three to nine-fold increase in hypoglycemic events, most of which occur at night (L. Y. Dawson, Clinical Diabetes, 11:88–96,1993) and sometimes can lead to loss of consciousness and convulsions. It has been found that severe hypoglycemic events seem to occur more often at night while the patient is asleep rather than during the day. When awake, diabetic patients can feel hypoglycemic reactions beginning, and can treat themselves with sugar in order bring their blood sugar levels back into the normal range. When asleep, patients do not have the awareness, therefore the risk of hypoglycemia is much higher during this time.

The use of cornstarch to combat hypoglycemia has also been tried. It has been found that protection against low blood sugar was provided for up to 6 to 8 hours after ingestion of uncooked starch (J. I. Woltsdorf, et al. Am. J. Clin. Nutr. , 51:1051–7, 1990). However, the dosage of cornstarch used for this treatment was 1.75 grams per kilogram of body weight. This dosage is much higher than can be tolerated by a patient with diabetes mellitus. It has been found that the cornstarch did little to prevent hypoglycemia (M. T. Ververs, et al., Eur. J. Clin Nutr., 47:268–73, 1983).

Diet has always been considered the most important factor in the management of diabetes even though insulin may be life saving for some.

Except for some restrictions and modifications the diabetes diet is not different from the diet of someone who does not have diabetes. The major principle is to modify the caloric intake keeping in view the height, weight and sex of the individual.

The dietary advice with regard to carbohydrate intake was concerned only with the amount or proportion of simple and complex carbohydrates. In fact both the type and form of carbohydrates have varying effects on blood sugar response.

It has been found that complex carbohydrates or starches such as rice or potato were believed to be slowly digested and absorbed causing only a small rise in blood glucose level. On the other hand, simple carbohydrates such as glucose, lactose and the like, were assumed to be readily digested, absorbed and producing large and rapid increases in blood glucose levels. Hence diabetics were advised to avoid taking simple sugars.

Diabetes is primarily a disorder of carbohydrate metabolism as stated earlier. However, the real danger of diabetes does not result in impaired carbohydrate metabolism but from impaired fat metabolism which follows disturbances of the carbohydrate metabolism.

The source of carbohydrates in the diet has a significant influence on lipid(fat) metabolism in a human being. The amount of sucrose is increased and the quantity of complex carbohydrates is decreased, the concentration of cholesterol and more particularly of Triglycerides increases which has a correlation between blood lipid concentration and impaired glucose tolerance.

Thus the need exists for a better method for treating hypoglycemia including a product to overcome the above-mentioned drawbacks.

According to one aspect of this invention, blood sugar levels in patients with diabetes mellitus are regulated and controlled by ingesting a therapeutic herbal composition.

Plants are part and parcel of human society from the dawn of civilization and extensive use of *Dolichos biflorus* as a food for both animals and human beings is known. It is used as a feed for cattle and horses. Stems, leaves and split husks are also used as cattle feed. The seeds are cooked before being used as a feed.

The seeds are consumed by humans after cooking or frying. They are eaten whole or after grinding into a meal, unlike other seeds which are consumed after splitting.

SUMMARY OF THE INVENTION

There is a desperate need to develop strategies to diminish diabetes while continuing to intensely manage diabetes.

It is very important to have an aggressive therapy for the prevention and control of diabetes. The main object of the present invention is to provide therapy to maintain and prolong a healthy, productive and successful life.

One of the important objects of the present invention is that the present invention is a 100% herbal medicine and no synthetic chemicals are used, even as preservatives to increase the shelf life of the invention. The naturally occurring constituents of the present invention act as preservatives.

The object of the invention is a product prepared from the seeds of *Dolichos biflorus* that can be used to treat diabetes.

A further object of the present invention is to have a product having a shelf life of more than a year.

Another object of the present invention is that the product is nontoxic in normal use.

Another objective of the present invention is to treat diabetes by treating the defect in metabolism, preserving pancreatic function and promoting psychological adjustments.

DETAILED DESCRIPTION OF THE INVENTION

The present invention relates to a therapeutic product processed from the seed of a plant from the family Leguminosea whose fibers effect the blood sugar level by increasing the viscosity of the unstirred layer between food and the lining of the intestines and stomach thereby making the carbohydrates available for absorption at a slower rate.

The herb *Dolichos biflorus* which is a member of the family Leguminosea comprises naturally occurring essential components. The plant contains approximately 7.57% by weight of woody fiber and approximately 12.9% by weight of digestible carbohydrate.

The seed of this herb can be used as a valuable protein supplement.

The part of the herb *Dolichos biflorus* used in the production of the product of the subject invention is the seed and the constituents of the seed are proteins, starch, oil, fiber, ash, phosphoric acid and enzymes. In the seed:

The moisture is normally 4.30% to 10.25% by weight,

Ether extract: 0.65% to 1.84% by weight

Protein: 20.75% to 22.25% by weight (containing Nitrogen 3.32% to 3.56% by weight)

Soluble Carbohydrates: 56.04% to 63.20% by weight

Woody fiber: 4.85% to 5.50% by weight

Ash: 4.20% to 7.45% by weight (containing sand 0.72% to 1.70% by weight)

The constituents of a seed are typically 11.8% by weight of moisture, 22.0% by weight of crude protein, 0.5% by weight of fat, 3.1% by weight of mineral matter, 5.3% by weight of fiber, 57.3% by weight of carbohydrates, calcium 0.28% by weight, phosphorous 0.39% by weight, iron 7.6 mg, nicotonic acid 1.5 mg, carotene 119 mg per 100 g.

The sugar level in patients with diabetes mellitus is regulated and reduced by ingesting a therapeutic herbal composition which includes a slowly metabolized complex carbohydrate.

The present invention relates to an herbal anti-diabetic therapeutic product comprising:

from about 89.5–98.5% by weight of powdered inner seed of *Dolichos biflorus* and from about 2.5–10.5% by weight of powdered fibrous outer shell of the seed of *Dolichos biflorus* to reach 100% of the composition The product is subjected to a radiation for a period of 10–20 minutes to destroy microorganisms including bacteria.

The process for the manufacture of this novel product comprises the steps of:

Cleaning the seed using conventional techniques to remove the dust and other superfluous particles. The seeds can be cleaned by washing with water.

Drying of the seeds: After the seeds are washed, the seeds are dried. The process of drying is carried out at ambient temperatures. The outer shells are removed and the remaining part of the seeds are dried heating up to temperature of 40–55° C. The seeds can be placed in open pans for drying.

The drying process results in the changing of the color of seeds from brown to golden brown.

Cooling of the seeds: After the seeds are dried and their color changes to golden brown, the seeds are then cooled to ambient temperature.

Decortication of the shell from the seed: The shell is removed from the seeds by a conventional manner and are kept separately.

Crushing of the seeds in a pulverizer: The seeds without the shells are then crushed by conventional methods. A pulverizer can be used. The crushing of the seeds is up to 150–300 sieve size. The crushed/powdered seeds contain 18% by weight of natural protein.

Crushing of the shell: The removed shell is powdered. A pulverizer can also be used to powder the shell. The crushing of the outer shell is up to 100–250 sieve size maintaining the fibrous strength and length.

Mixing of the powdered/crushed seeds with the powdered shell: 10.5–2.5% by weight of the powdered shell is mixed with the finely powdered seeds. The mixing may be carried out in a conventional mechanical mixer at low RPM for approximately 35–60 for the time period of 30–45 minutes.

Treatment of mixture: The mixture after it is removed from the mechanical mixer is placed in a stainless steel air tight compartment or other suitable container and is exposed to infrared rays for the time period of 10–20 minutes. The purposes of the exposure to infrared radiation is to make the mixture germ free. Other types of radiation can be used for this purpose.

Packing of the said product: The infrared exposed mixture is removed from the compartment and may be packed.

It is preferred that the mesh size of the final product is 150–200.

1–2 teaspoons of the herbal anti-diabetic product is to be taken daily. In a preferred embodiment the product can be taken with any liquid or solid and with breakfast and dinner. The fibers of the mixture makes a sheath in the intestine to reduce the absorption of the carbohydrates and natural insulin into the blood stream. This enables energy to be sustained for a period of at least 3 to 4 hours. In another preferred embodiment, one teaspoon of the powder is administered before breakfast and a second teaspoon of the powder is administered after breakfast.

The product used in the present invention being a fibrous product the fibers of the product are indigestible and is useful in preventing constipation.

The effect of the diabetic powder remains for a longer time as compared to the conventional available medicine. The reason is after the intake of normal conventional medicine, the amount of left over insulin in the pancreas is absorbed very quickly in the blood stream as compared to the powder of this invention and hence the frequency of the intake of the powder is less.

EXAMPLE I

The seed of *Dolichos biflorus* is used for the preparation of an anti-diabetic therapeutic product, in the amounts of:

98.% by weight of powdered inner seed of *Dolichos biflorus*

2% by weight of powdered fibrous outer shell of the seed of said *Dolichos biflorus*.

The seeds are washed with water to remove the dirt or other foreign particles followed by the drying of the seed at ambient temperatures, followed by heating to 40–55° C. in open pans. The seed is allowed to cool to ambient temperatures. The outer shell is removed and the decorticated inner seed is ground to a mesh size of 150–250 followed by the crushing of the outer fibrous shell to a sieve size of the mesh of 100–200 without destroying the length of the fiber. The powdered inner seed and outer shell are mixed at the ratio of 98:2 and are exposed to infrared rays for 10–20 minutes before packing.

1–2 teaspoons of powder of the herbal antidiabetic product is to be taken on a daily basis. The product can be taken with any liquid or solid, and optionally with breakfast and dinner.

EXAMPLE II

The seed of *Dolichos biflorus* is used for the preparation of an anti-diabetic therapeutic product, in the amount of:

97.5.% by weight of powdered inner seed of *Dolichos biflorus*

2.5% by weight of powdered fibrous outer shell of the seed of *Dolichos biflorus*.

The seeds are washed with water to remove the dirt or other foreign particles followed by the drying of the seed at ambient temperatures, followed by heating the seeds up to 45–55° C. in open pans. The seed is allowed to cool to ambient temperatures. The outer shell is removed and the decorticated inner seed is ground to a mesh size of 175–250 followed by the crushing of the outer fibrous shell to a sieve size of the mesh of 150–250 without destroying the length of the fiber. The powdered inner seed and outer shell are mixed at the ratio of 97.5:2.5 and is exposed to infrared rays for 10–20 minutes before packing.

1–2 teaspoons full of powder if the herbal anti-diabetic product is to be taken daily. The mixture can be taken with any liquid or solid diet and with breakfast and dinner.

EXAMPLE III

A study was conducted to determine the effect of the present composition on blood glucose, serum cholesterol and triglyceride levels of newly diagnosed diabetics. The therapeutic composition is administered as part of an overall program of treatment, including control of diet. The results showed that the product was very effective with no side effects.

During various trials conducted both on patients taking insulin and on patients taking oral medicine, the blood sugar level has come down in both the cases. As a result of the usage of this powder, the normal medicine they were taking were eliminated and the blood sugar level was controlled between 145–160. The dosage of intake of the powder is same for all types of patients. The frequency of intake of the powder varies with reference to the blood sugar level.

ADVANTAGES OF THE PRESENT INVENTION

1) The therapeutic medicinal product is derived from naturally occurring plants, and the product has no or minimal side-effects. No synthetic chemicals are used for the preservation or synthesis of the end product.

2) One of the components of the product is fiber, which results not only in the reduction of natural insulin level but also helps in preventing constipation.

3) *Dolichos biflorus* is cultivated in abundance, it is very cost effective and is affordable.

4) The product is completely an herbal product where no synthetic chemicals are used even as a preservatives, as the constituents of the product itself acts as a preservative.

5) Besides having no side effects the present herbal therapeutic product conserves carbohydrate metabolism thus giving the patient more energy with minimum consumption of carbohydrates.

I claim:

1. An herbal anti-diabetic therapeutic product comprising:
   from about 89.5–98.5% by weight of powdered inner seed of *Dolichos biflorus* and
   from about 1.5 to 10.5% by weight of powdered fibrous outer shell of the seed of *Dolichos biflorus*.

2. The product of claim 1 wherein the product is exposed to radiation for a period of from 10 to 20 minutes.

3. The product as claimed in claim 1, wherein said powdered inner seed is meshed to 150 to 300 sieve size.

4. The product as claimed in claim 1, wherein the powdered fibrous outer shell is meshed to 100 to 250 sieve size.

5. The product as claimed in claim 1, having a shelf life of more than one year.

6. The product as claimed in claim 2, wherein the radiation is infra-red rays.

7. A process for the manufacture of an herbal anti-diabetic therapeutic product, comprising cleaning seed of *Dolichos biflorus*, drying the seed at ambient temperature, drying at a temperature of 40–55° C., cooling said seeds at ambient temperature, decorticating the outer shell of the seed, crushing the seed to form a powder, crushing the shell to form a powder, mixing the powders of seed and shell in the ratio of 89.5–98.5%:10.5–1.5% and exposing the mixture to radiation.

8. The process of claim 7 wherein the mixture is exposed to infra-red rays.

9. The process of claim 7 wherein the mixture is exposed to radiation for a period of 10–20 minutes.

* * * * *